(12) United States Patent
Hirose et al.

(10) Patent No.: US 10,188,306 B2
(45) Date of Patent: Jan. 29, 2019

(54) CARDIAC POTENTIAL DETECTION DEVICE AND CARDIAC POTENTIAL DETECTION METHOD

(71) Applicant: Panasonic Intellectual Property Management Co., Ltd., Osaka (JP)

(72) Inventors: Yoshifumi Hirose, Kyoto (JP); Shoichi Araki, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/846,715

(22) Filed: Dec. 19, 2017

(65) Prior Publication Data

US 2018/0103866 A1      Apr. 19, 2018

Related U.S. Application Data

(63) Continuation of application No. PCT/JP2016/002880, filed on Jun. 15, 2016.

(30) Foreign Application Priority Data

Jun. 25, 2015    (JP) .................................. 2015-127161

(51) Int. Cl.
*A61B 5/04* (2006.01)
*A61B 5/0456* (2006.01)
(Continued)

(52) U.S. Cl.
CPC ........ *A61B 5/0456* (2013.01); *A61B 5/04085* (2013.01); *A61B 5/6893* (2013.01);
(Continued)

(58) Field of Classification Search
CPC .. A61B 5/0456; A61B 5/04085; A61B 5/6893
See application file for complete search history.

(56) References Cited

U.S. PATENT DOCUMENTS 4,000,461 A    12/1976   Barber et al.
6,438,411 B1 *  8/2002   Guttman ............. A61B 5/0428
                                                              600/521
(Continued)

FOREIGN PATENT DOCUMENTS

JP     50-61889       5/1975
JP     2006-523126    10/2006
(Continued)

OTHER PUBLICATIONS

International Search Report dated Sep. 20, 2016 in International (PCT) Application No. PCT/JP2016/002880.

*Primary Examiner* — Rex R Holmes
(74) *Attorney, Agent, or Firm* — Wenderoth, Lind & Ponack, L.L.P.

(57) ABSTRACT

A cardiac potential detection device for detecting R-waves from an electrocardiographic waveform includes a plurality of electrodes, a detector, and a control unit. The detector detects an input voltage applied from the electrodes. The control unit identifies an R-wave based on the input voltage detected by the detector, but suspends identifying R-waves in a detection-suspension period including a period in which the input voltage exceeds a predetermined threshold.

9 Claims, 18 Drawing Sheets

(51) Int. Cl.
*A61B 5/0408* (2006.01)
*A61B 5/00* (2006.01)

(52) U.S. Cl.
CPC .......... *A61B 5/7207* (2013.01); *A61B 5/6804* (2013.01); *A61B 5/6823* (2013.01)

(56) References Cited

U.S. PATENT DOCUMENTS

| | | | |
|---|---|---|---|
| 2003/0069609 A1 | 4/2003 | Thompson | |
| 2004/0049120 A1* | 3/2004 | Cao | A61B 5/0456 600/521 |
| 2004/0171953 A1 | 9/2004 | Hemming et al. | |
| 2006/0235476 A1 | 10/2006 | Gunderson et al. | |
| 2007/0255150 A1 | 11/2007 | Brodnick | |
| 2009/0292331 A1 | 11/2009 | Gunderson et al. | |
| 2010/0204552 A1 | 8/2010 | Yamamoto et al. | |
| 2013/0060117 A1 | 3/2013 | Gunderson et al. | |
| 2015/0005608 A1* | 1/2015 | Evans | A61B 5/0428 600/383 |

FOREIGN PATENT DOCUMENTS

| | | |
|---|---|---|
| JP | 2008-104641 | 5/2008 |
| JP | 2008-536633 | 9/2008 |
| WO | 2004/078258 | 9/2004 |
| WO | 2006/113698 | 10/2006 |
| WO | 2009/016886 | 2/2009 |
| WO | 2013/180286 | 12/2013 |

* cited by examiner

CARDIAC POTENTIAL DETECTION DEVICE AND CARDIAC POTENTIAL DETECTION METHOD

BACKGROUND

1. Technical Field

The present disclosure relates to devices for detecting R-waves from an electrocardiographic waveform.

2. Description of the Related Art

Patent Literature 1 discloses a waveform detector that blocks signals from an electronic cardiac pacer or other similar device. This waveform detector includes a pacer signal detector, an amplitude discriminator, a short-time discriminator, and a long-time discriminator. The pacer signal detector detects signals greater than electrocardiographic signals. The amplitude discriminator prevents signals other than electrocardiographic signals from being applied to the short-time discriminator. The short-time discriminator receives a potential triggered by an R wave and generates a pulse signal. The long-time discriminator receives the output of the short-time discriminator and outputs a rectangular pulse signal. This reduces falsely detecting cardiac pulses as R-waves from the electronic cardiac pacer.

CITATION LIST

Patent Literature

PTL 1: Japanese Unexamined Patent Application Publication No. S50-061889

SUMMARY

The present disclosure provides a cardiac potential detection device effectively reducing false detection of R-waves.

The cardiac potential detection device according to the present disclosure for detecting R-waves from an electrocardiographic waveform includes a plurality of electrodes, a detector, and a control unit. The detector detects an input voltage applied from the electrodes. The control unit identifies an R-wave based on the input voltage detected by the detector, but suspends identifying R-waves in a detection-suspension period including a period in which the input voltage exceeds a predetermined threshold.

In the cardiac potential detection method according to the present disclosure, an input voltage applied from a plurality of electrodes is detected, and an R-wave is identified based on the input voltage, but identification of R-waves is suspended in a period in which the input voltage exceeds a predetermined threshold.

The cardiac potential detection device according to the present disclosure effectively reduces false detection of R-waves.

DETAILED DESCRIPTION

An exemplary embodiment will be described in detail as follows with reference to the accompanying drawings. In the exemplary embodiment, the description of well-known matter and of substantially the same configuration as described earlier may be omitted to avoid redundancy and help those skilled in the art understand them easily.

Note that the attached drawings and the following description are provided to make those skilled in the art fully understand the present disclosure, and are not intended to limit the claimed subject matter.

Exemplary Embodiment

The cardiac potential detection device according to an exemplary embodiment will now be described with reference to FIGS. 1 to 11.

Figure 1:
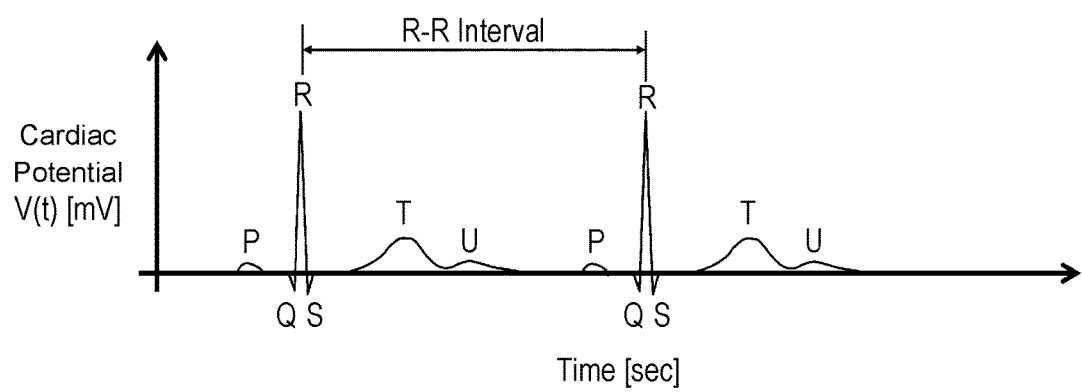
FIG. 1 is a schematic diagram of an example of an electrocardiographic waveform.

FIG. 1 shows an example of an electrocardiographic (hereinafter, ECG) waveform. In general, an ECG waveform includes P-, Q-, R-, S-, T-, and U-waves occurring in each heartbeat. Of these waves, the R-wave has a large amplitude and changes steeply per unit time, and therefore, is used for heartbeat detection.

R-wave detection is performed by identifying the appearance time of an R-wave. For example, the absolute value of the differential value of an ECG waveform can be regarded as a feature, and the time when the peak of the feature appears may be approximately determined to be the appearance time of the R-wave. The time when the peak of the feature appears can be, for example, the time when the feature is maximum in a predetermined period of time starting from the time the feature exceeds a predetermined threshold (an R-wave detection threshold). A more accurate appearance time of an R-wave may be determined by identifying the time when the cardiac potential is maximum in a predetermined period of time starting from the time the peak of the feature appears. The difference between two consecutively detected R-waves is referred to as an RR interval, and is used to calculate the heart rate.

Figure 2:
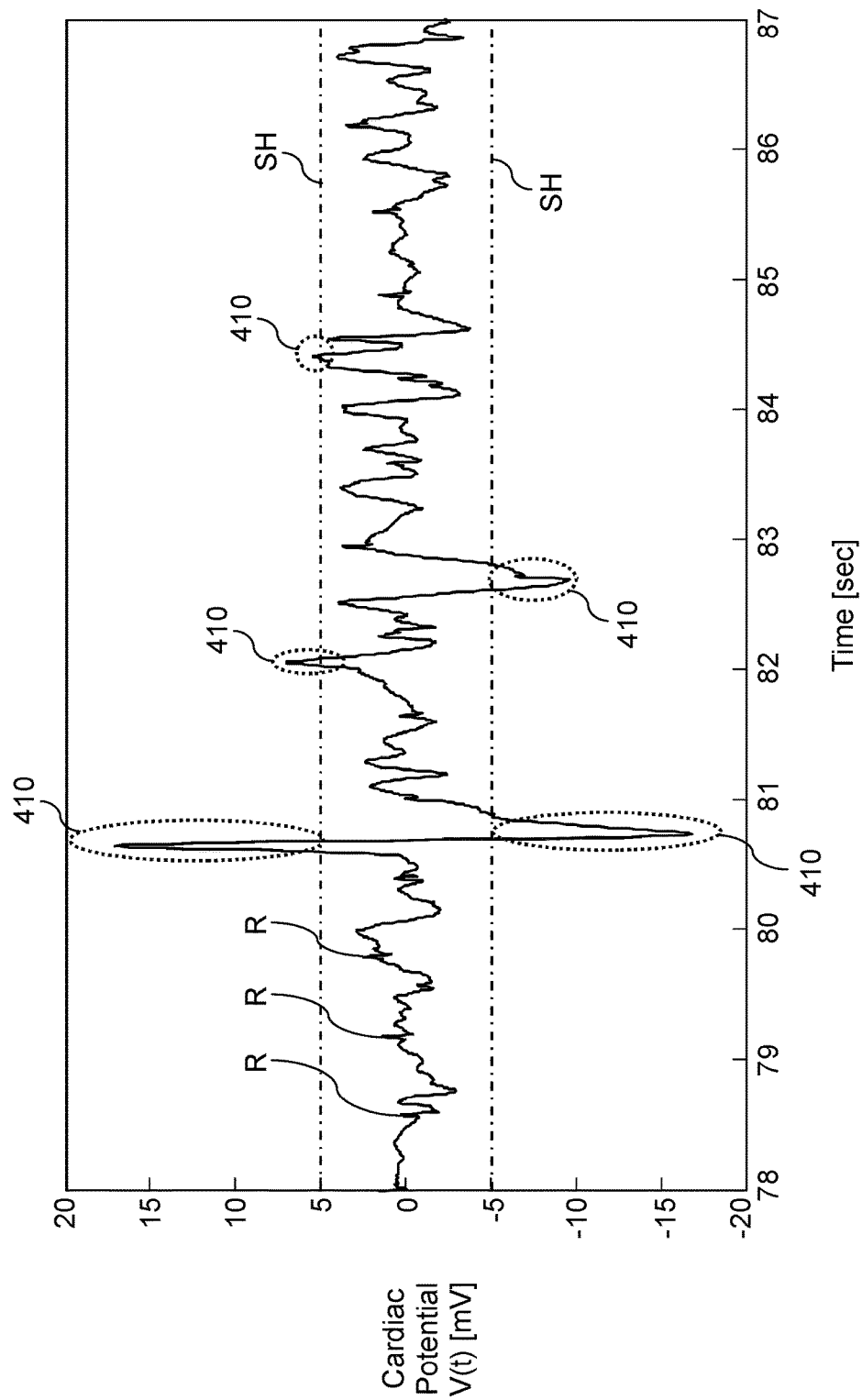
FIG. 2 is an electrocardiogram measured using electrodes.

FIG. 2 shows a voltage waveform measured as an ECG waveform when the user bends his/her body sideways with a belt having electrodes pasted thereon around his/her chest. When the condition of contact between the electrodes and the user's body changes as the user moves his/her body, the voltage changes steeply. The voltage includes noise with a larger amplitude than R-waves as shown in FIG. 2. This indicates that it is difficult to correctly identify R-waves while the user is moving. In and near abnormal potential generation periods 410 during which a large noise is generated, R-waves are difficult to detect, and what is worse, voltage waveforms other than R-waves may be falsely detected as R-waves. Abnormal potential generation period 410 is defined as a period exceeding a predetermined threshold SH. The threshold SH is determined adaptively based on the obtained voltage waveform. For example, if the ECG waveform estimated from the obtained voltage waveform has a large amplitude, the electrodes seem to be in good contact with the user's body. In this case, the predetermined threshold SH is set to a large value.

1-1. Configuration

Figure 3:
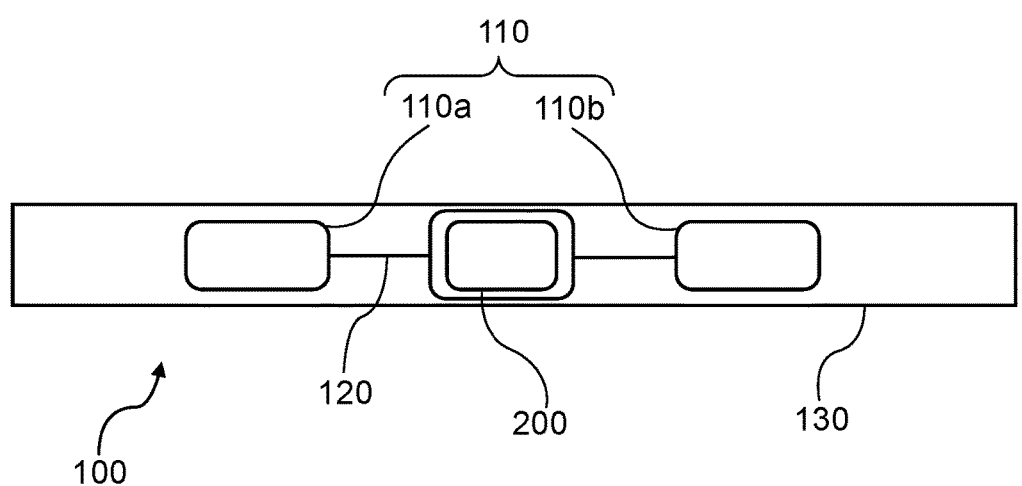
FIG. 3 is a schematic diagram of a cardiac potential detection device according to an exemplary embodiment.

FIG. 3 is a schematic diagram of cardiac potential detection device 100 according to the exemplary embodiment. Device 100 includes electrodes 110 consisting of right electrode 110a and left electrode 110b, wiring 120, belt (attachment medium) 130, and controller 200.

Right electrode 110a and left electrode 110b, which are brought into direct contact with the human body, can be made of any conductive material. In the exemplary embodiment, electrodes 110 are made of conductive rubber to achieve close contact with the human body. Alternatively, electrodes 110 may be made of conductive fiber. Right electrode 110a and left electrode 110b are attached on both sides of the user's heart so as to obtain the voltage waveform of a cardiac potential (hereinafter, also referred to as the ECG waveform). The cardiac potential can be obtained from the potential difference between the two electrodes 110a and 110b. Alternatively, it is possible to provide a reference electrode so as to obtain the potential differences between the reference electrode and right electrode 110a and between the reference electrode and left electrode 110b, thereby obtaining the potential difference between right and left electrode 110a and 110b. The positions of electrodes 110 are not limited to those shown in FIG. 3; the ECG waveform can be obtained by using any well-known electrode layout.

Electrodes 110 are attached to belt (attachment medium) 130. The user wears belt 130 around the chest in such a manner that right electrode 110a and left electrode 110b come into contact with the skin, thereby obtaining the ECG waveform. Electrodes 110 may be attached to other attachment media than belt 130, such as a stretchable T shirt or corset in such a manner that electrodes 110 are located on the user's chest. Alternatively, electrodes 110 may be coated with adhesive gel and pasted to the user's skin. Further alternatively, electrodes 110 may be attached to a steering wheel or other devices which the user can grip with both hands.

Controller 200 receives an ECG waveform obtained as the potential difference between right electrode 110a and left electrode 110b, and detects R-waves from the ECG waveform.

Figure 4:
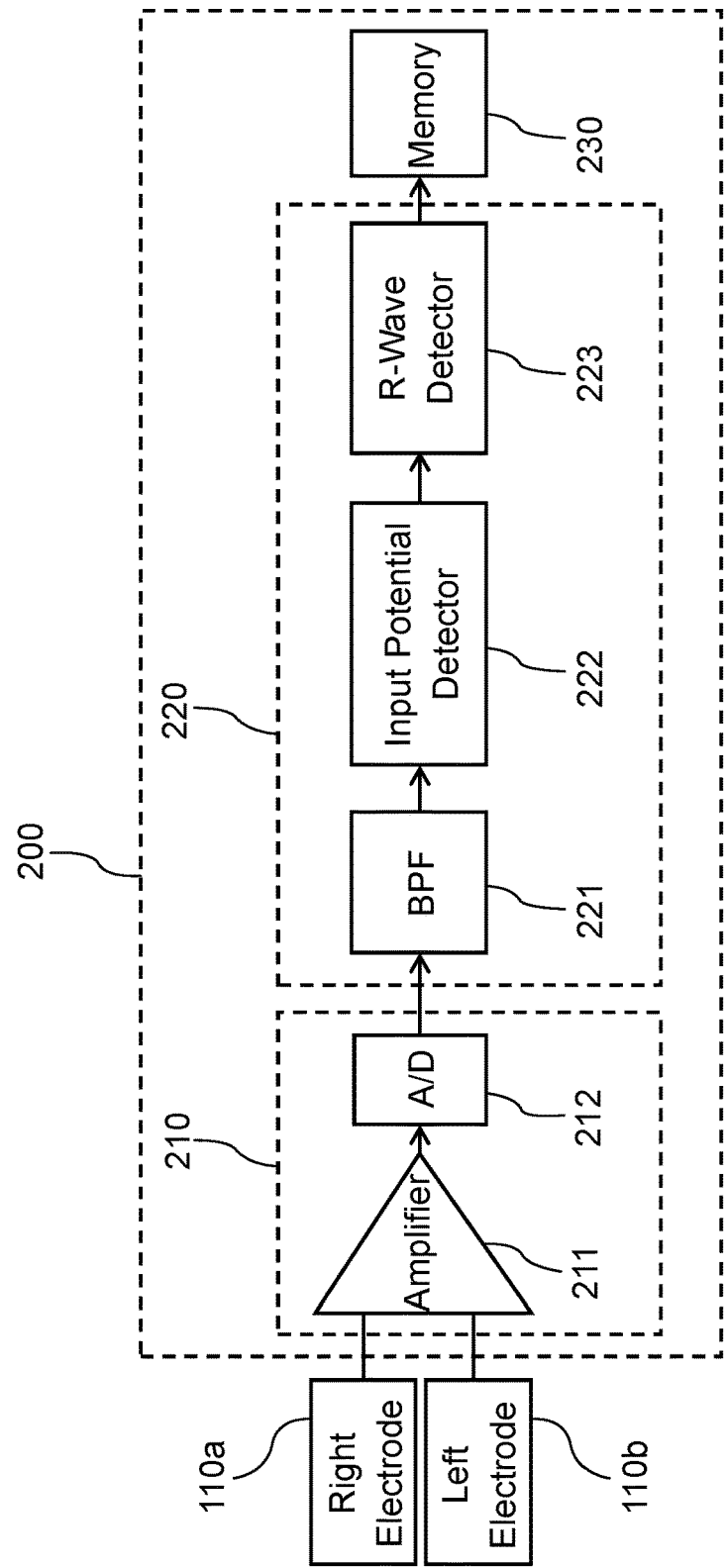
FIG. 4 is a block diagram of a controller in the cardiac potential detection device according to the exemplary embodiment.

FIG. 4 is a block diagram of controller 200 in cardiac potential detection device 100 according to the exemplary embodiment. Controller 200 includes analog front end (AFE) 210, control unit 220, and memory 230. AFE 210 includes amplifier 211 for amplifying a cardiac potential obtained by electrodes 110, and A/D converter 212 for AD-converting the amplified cardiac potential. AFE 210 is an analog circuit for coupling electrodes 110 and control unit 220. Control unit 220 includes band pass filter (BPF) 221, input potential detector 222, and R-wave detector 223. Thus, BPF 221 bandlimits the AD-converted signal in order to keep the heartbeat component intact in the signal. Input potential detector 222 detects whether the bandlimited ECG waveform is an abnormal potential. R-wave detector 223 detects R-waves from the ECG waveform that has been determined not to be an abnormal potential. BPF 221 bandlimits the acquired cardiac potential V(t). The passband is not particularly limited as long as it can keep the heartbeat component intact; a preferred passband is, for example, about one to several tens of hertz. In the following description, a bandlimited ECG waveform, which is an input to both detectors 222 and 223, is also referred simply as an ECG waveform. Input potential detector 222 detects an abnormal potential, which occurs, for example, when electrodes 110 are removed from the user's skin. This detection will be detailed later. R-wave detector 223 has an R-wave detection threshold by which R-wave candidates are detected from the ECG waveform. If the feature of the ECG waveform exceeds the R-wave detection threshold, R-wave detector 223 detects the feature as an R-wave candidate. From the detected R-wave candidates, R-wave detector 223 further detects an R-wave candidate that meets predetermined requirements. R-wave detector 223 then identifies, as the appearance time of the R-wave, the time when the peak of the feature of the ECG waveform appears in the part of the ECG waveform that corresponds to the R-wave. The value of the feature of an ECG waveform is affected by various factors (e.g., the user's physical condition, the condition of contact between electrodes 110 and the user's body, and the user's physical characteristics). For example, when the user's body and electrodes 110 are in good contact with each other, the obtained ECG waveform has a larger amplitude than when they are not in good contact with each other. Furthermore, the condition of contact between the user's body and electrodes 110 varies with time. Consequently, the amplitude of the obtained ECG waveform varies with time, so that the R-wave detection threshold suitable for R-waves detection also varies with time. Therefore, R-wave detector 223 updates the R-wave detection threshold based on the value of the peak of the feature of the voltage waveform corresponding to the most recently detected R-wave. Memory 230 stores the appearance times of the R-waves identified by control unit 220. Memory 230 may further store the time difference (RR interval) between the most recently detected R-wave and the immediately preceding detected R-wave. Alternatively, cardiac potential detection device 100 may include a transmitter that transmits the appearance times of R-waves to an external device such as a display device or a server instead of storing them in memory 230.

1-2. Operation

The operation of the above-described cardiac potential detection device 100 will now be described.

Figure 5:
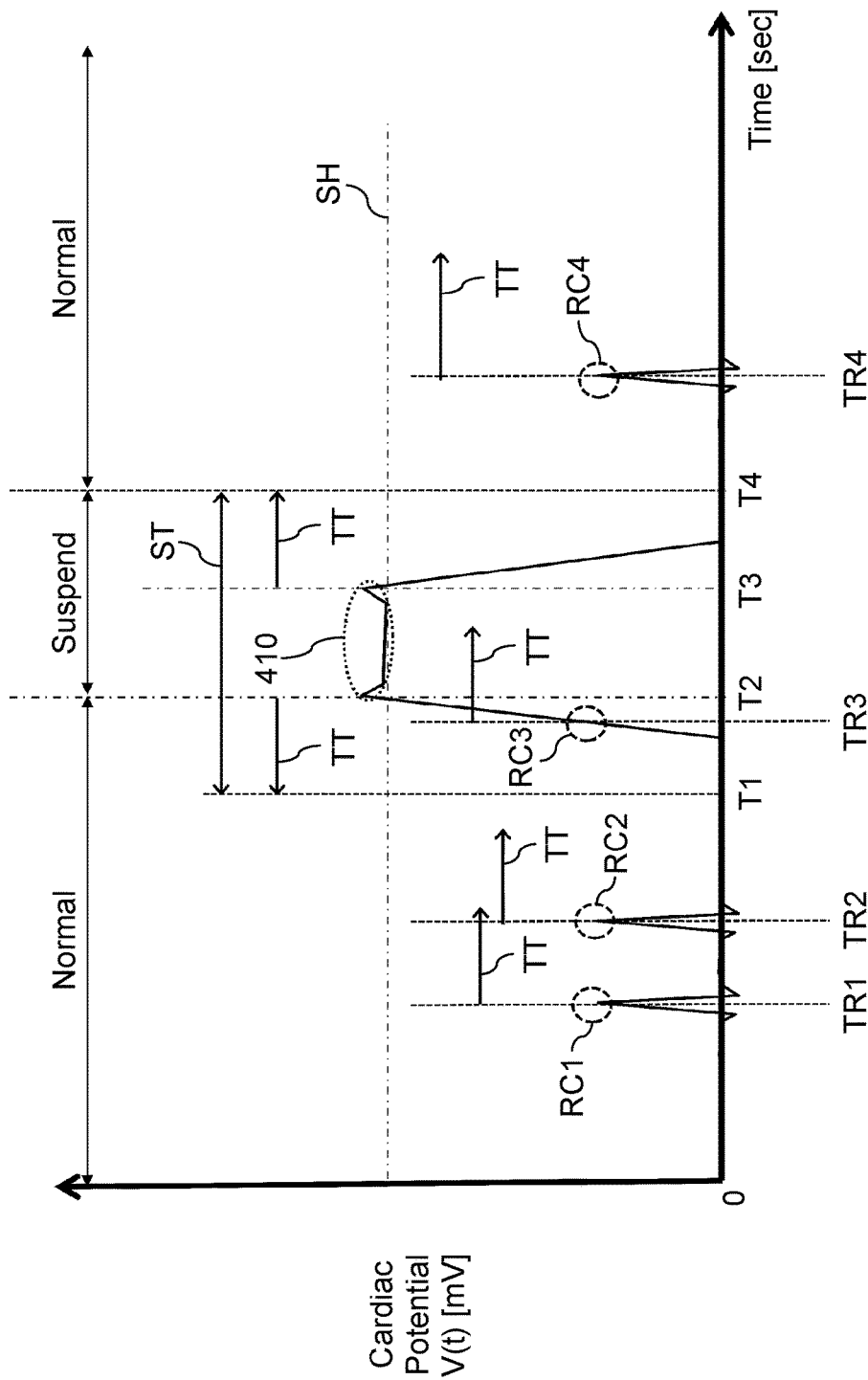
FIG. 5 is a schematic diagram of an operational example of the cardiac potential detection device according to the exemplary embodiment.

Cardiac potential detection device 100 according to the present disclosure suspends R-wave detection in abnormal potential generation periods 410 and in transient period TT, which occurs before and after each period 410. The period to suspend R-wave detection is referred to as a detection-suspension period ST. In the present exemplary embodiment, the transient period TT is 500 ms. FIG. 5 is a schematic diagram of an operational example of cardiac potential detection device 100 according to the exemplary embodiment.

In the detection-suspension period ST, R-wave detection is suspended in abnormal potential generation period 410 and the subsequent transient period TT. In the remaining period, R-wave detection is performed at predetermined time intervals. In the present exemplary embodiment, R-wave detection is suspended also in the transient period TT occurring before the start of abnormal potential generation period 410. However, this transient period TT occurs before the detection of an abnormal potential. In other words, even of a voltage waveform that is to be determined as an R-wave is detected, it cannot be confirmed, at the time of the R-wave detection, whether the R-wave detection time is within the detection-suspension period. Therefore, upon detecting a voltage waveform that is determined to be an R-wave unless the R-wave detection time is within the detection-suspension period ST, R-wave detector 223 stores, as an R-wave candidate RC, a detection time TR at which the peak of the voltage waveform is detected. If no abnormal potential is detected in the period from the detection time TR of the R-wave candidate RC until the transient period TT expires, the R-wave candidate RC is confirmed as an R-wave. Meanwhile, if an abnormal potential is detected in the transient period TT, the R-wave candidate RC is abandoned. This is how R-wave detection is suspended in the transient period TT occurring before the occurrence of an abnormal potential.

Figure 6:
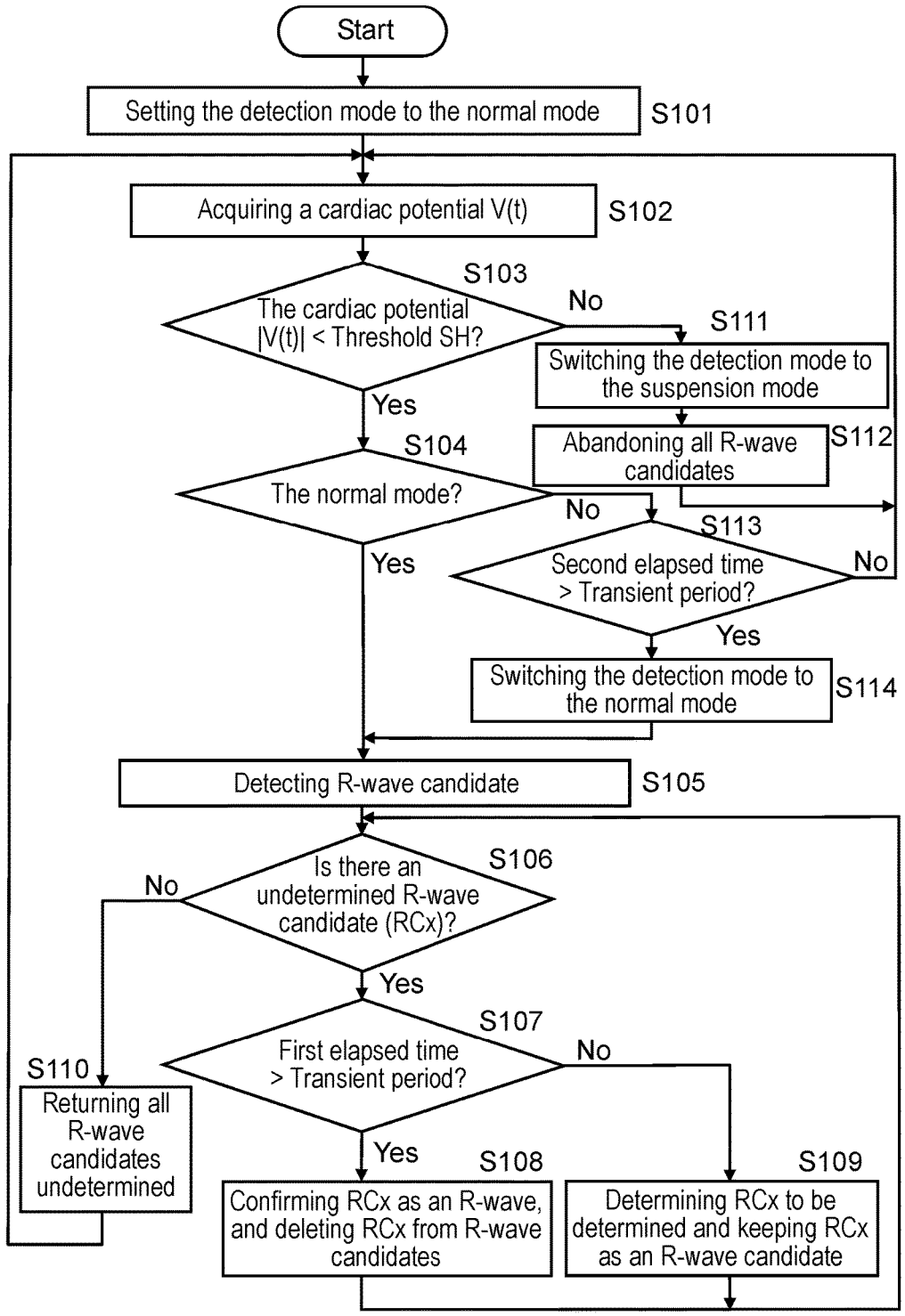
FIG. 6 is a flowchart showing the operation of the cardiac potential detection device according to the exemplary embodiment.

Detailed operation of the exemplary embodiment will now be described with reference to the diagram of FIG. 5 and the flowchart of FIG. 6.

First, in Step S101, input potential detector 222 sets the detection mode to a normal mode, which is the initial state. Detector 222 has the normal mode in which the detection of R-wave candidates RC is performed, and a suspension mode in which the detection of R-wave candidates RC is not performed. Thus, whether the detection of R-wave candidates RC is performed is determined by the detection mode of detector 222.

Next, in Step S102 R-wave detector 223 acquires a cardiac potential V(t) at time t, which is bandlimited by BPF 221. To be more specific, amplifier 211 amplifies the potential difference between right electrode 110a and left electrode 110b, and A/D converter 212 AD-converts the amplified potential difference so as to acquire the cardiac potential V(t).

Next, in Step S103 input potential detector 222 compares the absolute value of the cardiac potential V(t) with the predetermined threshold SH. The threshold SH is determined based on the voltage range of amplifier 211 or A/D converter 212. For example, if the voltage range of A/D converter 212 is ±20 mV, it is determined whether the absolute value of the cardiac potential V(t) is greater than 20 mV. The threshold SH does not necessarily have to be in the voltage range, and may be the multiple of the voltage range and a predetermined rate. The predetermined rate can be determined considering the features of BPF 221, and can be, for example, 90%. Alternatively, the rate may be a value that can be obtained with general R-waves (e.g., several millivolts). If the absolute value of the acquired cardiac potential V(t) is smaller than the threshold SH (Yes in Step S103), the process goes to Step S104. Meanwhile, if the absolute value is not less than the threshold SH (No in Step S103), the process goes to Step S111.

Next, in Step S104 input potential detector 222 determines whether the detection mode is the normal mode. If it is the normal mode (Yes in Step S104), the process goes to Step S105. Meanwhile, if it is not the normal mode (No in Step S104), the process goes to Step S113.

Next, in Step S105 R-wave detector 223 detects R-wave candidates based on the cardiac potential V(t). R-wave detector 223 regards the absolute value of the differential value of the ECG waveform as the feature, and identifies, from a certain period, the detection time TR at which the peak of the feature appears. If the value of the peak of the feature exceeds the R-wave detection threshold, the peak is stored as the R-wave candidate RC. Alternatively, the detection time TR at which the peak of the feature appears may be the time at which the feature is maximum in the period of time after the feature exceeds the R-wave detection threshold until a predetermined time expires. The R-wave detection threshold is adaptively determined based on the maximum value of the feature (for example, 60% of the maximum value) in a predetermined period of time (e.g., several seconds) including the R-wave candidate RC. This enables the R-wave detection threshold to be a value suitable for R-wave detection, along with the temporal change of the amplitude of the ECG waveform. In the example of the ECG waveform shown in FIG. 5, R-wave candidates RC (RC-1 to RC-4) are identified when the detection mode is the normal mode. Furthermore, detection times TR (TR-1 to TR-4), which correspond to R-wave candidates RC (RC-1 to RC-4), respectively are stored in memory 230 as the times indicating the peaks of the features calculated based on the time waveform of the cardiac potential.

Next, in Step S106 R-wave detector 223 determines whether there is an undetermined R-wave candidate. If there is an undetermined R-wave candidate (Yes in Step S106), this candidate is made to be a target R-wave candidate RCx, and the process goes to Step S107. Meanwhile, if there is no undetermined R-wave candidate (No in Step S106), the process goes to Step S110.

In Step S107, R-wave detector 223 determines whether a first elapsed time (t-TR) exceeds the transient period TT with respect to the target R-wave candidate RCx. The first elapsed time indicates the time elapsed from a detection time TRx corresponding to the target R-wave candidate RCx up to the present time t. If the first elapsed time exceeds the transient period TT, or in other words, if the transient period TT or more time has elapsed since the detection of the target R-wave candidate RCx, the process goes to Step S108. In this case, it is determined that an abnormal potential has not been detected in the period from the detection time TRx at which the target R-wave candidate RCx is detected until the transient period TT expires. If the first elapsed time does not exceed the transient period TT, the process goes to Step S109.

Next, in Step S108 the target R-wave candidate RCx is confirmed as an R-wave because no abnormal potential has been detected in the transient period TT occurring before and after the detection time TRx at which the target R-wave candidate RCx is detected. To be more specific, R-wave detector 223 confirms the target R-wave candidate RCx as an R-wave and stores this R-wave and the corresponding detection time TRx into memory 230. R-wave detector 223 further stores in memory 230 the RR interval, which is the difference between the detection time TRx and the detection time TR corresponding to the latest R-wave of all R-waves confirmed before the target R-wave candidate RCx. Furthermore, R-wave detector 223 deletes the confirmed target R-wave candidate RCx from the R-wave candidates. In the example of FIG. 5, R-wave candidates RC-1, RC-2, and RC-4 are confirmed as R-waves in Step S108 after the transient period TT has elapsed since the detection times TR-1, TR-2, and TR-4, respectively.

In Step S109 R-wave detector 223 determines that the target R-wave candidate RCx has been determined and keeps it as an R-wave candidate. After this, the process goes back to Step S106 where the undetermined R-wave candidates are subjected to the same procedure.

In Step S110 all R-wave candidates are returned undetermined, and the process goes back to Step S102 where the operation of acquiring a cardiac potential V(t) is continued.

The following is a description of the case where in Step S103 the absolute value of the acquired cardiac potential V(t) is greater than the threshold SH (No in Step S103). If the absolute value is greater than the threshold SH, the detected ECG waveform is expected to be greatly affected by noise. This ECG waveform is also considered to be greatly affected by noise during the period before and after the period in which the absolute value of the cardiac potential V(t) is greater than the threshold SH. In these periods of strong noise influence, it is preferable to suspend R-wave detection because R-waves are likely to be identified with lower accuracy.

In Step S111 input potential detector 222 switches the detection mode to the suspension mode, and suspends the detection of R-wave candidates. In the example shown in FIG. 5, the absolute value of the cardiac potential V(t) exceeds the threshold SH at time T2, so that the detection mode is switched to the suspension mode to suspend the detection of R-wave candidates in Step S111. Thus, the time T2 corresponds to the start of abnormal potential generation period 410.

Next, in Step S112, R-wave detector 223 abandons all R-wave candidates, and the process goes back to Step S102. In the period from the time earlier than the start of abnormal potential generation period 410 by the transient period TT to the start of period 410 is included in the detection-suspension period ST. Therefore, the R-wave candidates detected in this period are abandoned without being detected as R-waves. In the example shown in FIG. 5, all R-wave candidates detected between time T1 and time T2 are abandoned. This means that R-wave candidate RC3 is abandoned.

Next, in Step S113 input potential detector 222 determines whether the second elapsed time exceeds the transient period TT. The second elapsed time indicates the period from the end of abnormal potential generation period 410 up to the present time t.

If the second elapsed time is equal to or less than the transient period TT, the process goes back to Step S102 to continue to acquire a cardiac potential. Meanwhile, if the second elapsed time exceeds the transient period TT (Yes in Step S113), input potential detector 222 determines that the transient period TT has elapsed since the end of abnormal potential generation period 410, and the process goes to Step S114.

In Step S114 input potential detector 222 switches the detection mode to the normal mode, and the process goes to Step S105.

In the example shown in FIG. 5, the second elapsed time (t-T3) is determined to have exceeded the transient period TT in Step S113 at time T4 when the transient period TT has elapsed since time T3, which is the last moment at which the absolute value of the cardiac potential V(t) exceeds the threshold SH. The process goes to Step S114. In Step S114 the detection mode is set to the normal mode, and the process goes to Step S105 where the detection of R-wave candidates is restarted.

Thus, R-wave detection is suspended not only in abnormal potential generation period 410 but also in the period before and after the period 410. This reduces falsely detecting, as R-waves, steep changes in the transient period TT in an ECG waveform.

1-3. Effects

Figure 7:
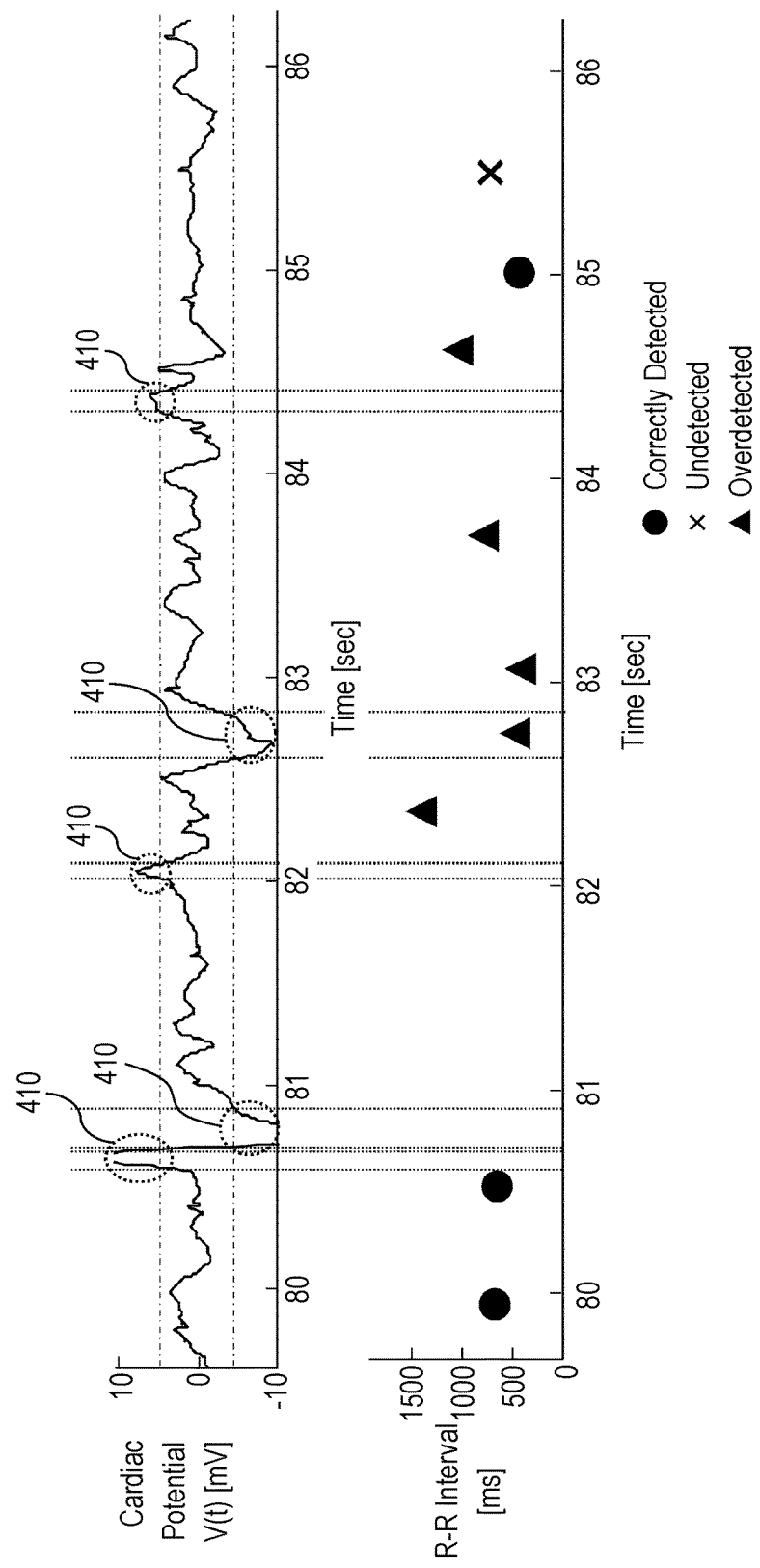
FIG. 7 shows an electrocardiographic waveform obtained in the exemplary embodiment and R-waves detected according to a conventional method.

FIG. 7 shows an ECG waveform obtained in the exemplary embodiment and R-waves detected without detecting an abnormal potential with the use of a threshold. In FIG. 7, five cases of R-wave overdetection (shown by triangles), which are due to changes in the condition of contact between of electrodes 110 and the user's body, occur near abnormal potential generation periods 410.

Figure 8:
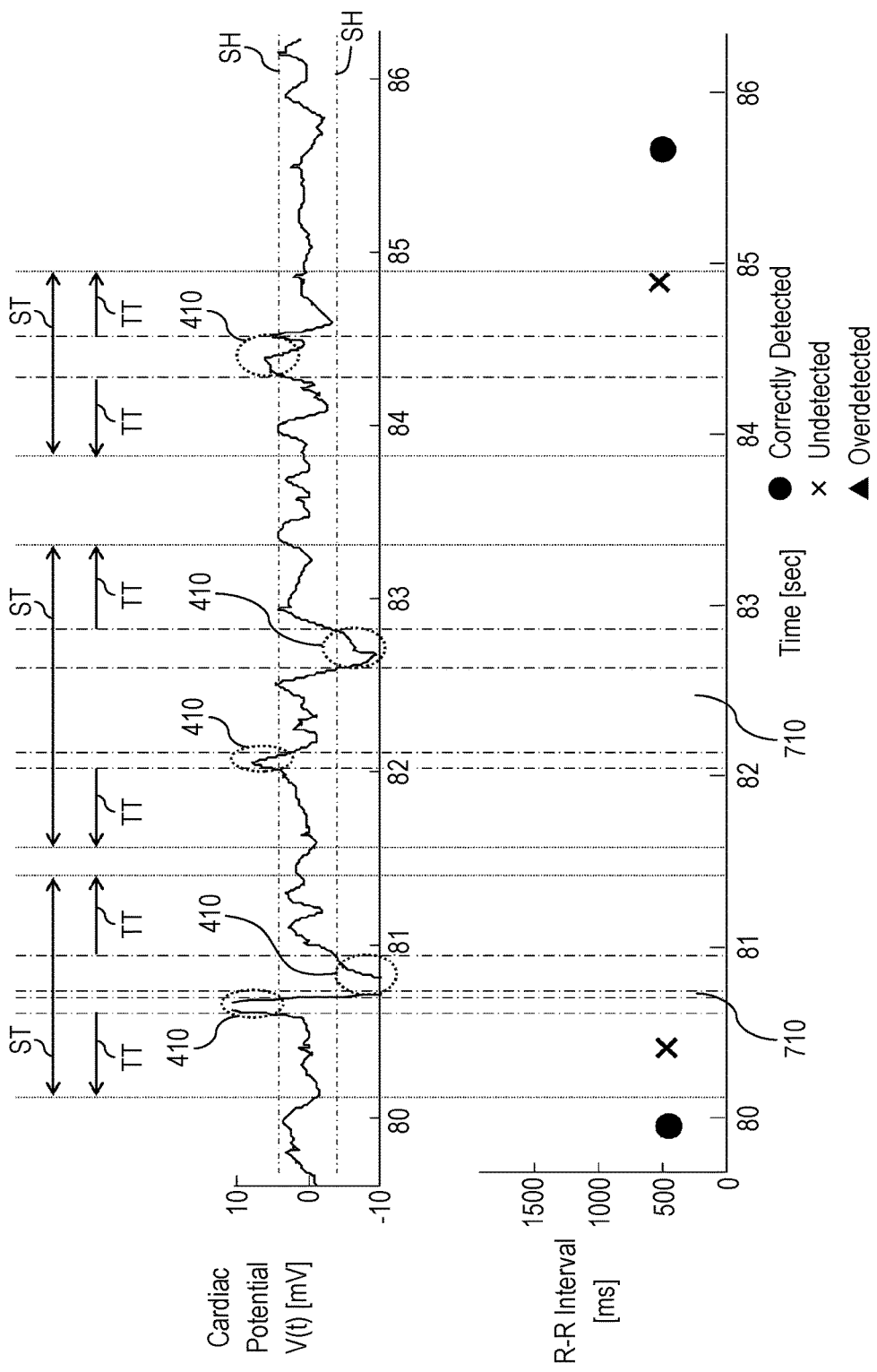
FIG. 8 shows an electrocardiographic waveform obtained in the exemplary embodiment and R-waves detected according to the present disclosure.

Meanwhile, FIG. 8 shows an ECG waveform obtained by cardiac potential detection device 100 according to the exemplary embodiment, and R-waves detected when R-wave detection is suspended in abnormal potential generation periods 410 and in a 500 ms transient period TT before and after each period 410. Thus, R-wave detection is suspended not only in abnormal potential generation periods 410 but also in the transient period TT before and after each period 410. In this case, the steep changes in the ECG waveform shown in FIG. 8, which are caused when the user moves physically, are treated as the detection-suspension period ST. As a result, R-wave detection is suspended to reduce R-wave overdetection. When the user wears the attachment equipped with electrodes around his/her body to measure an ECG waveform, R-wave detection is suspended in abnormal potential generation periods 410 and the transient period TT before and after each period 410. This reduces falsely detecting, as R-waves, steep changes in the ECG waveform, which are caused when the user moves physically.

Figure 9:
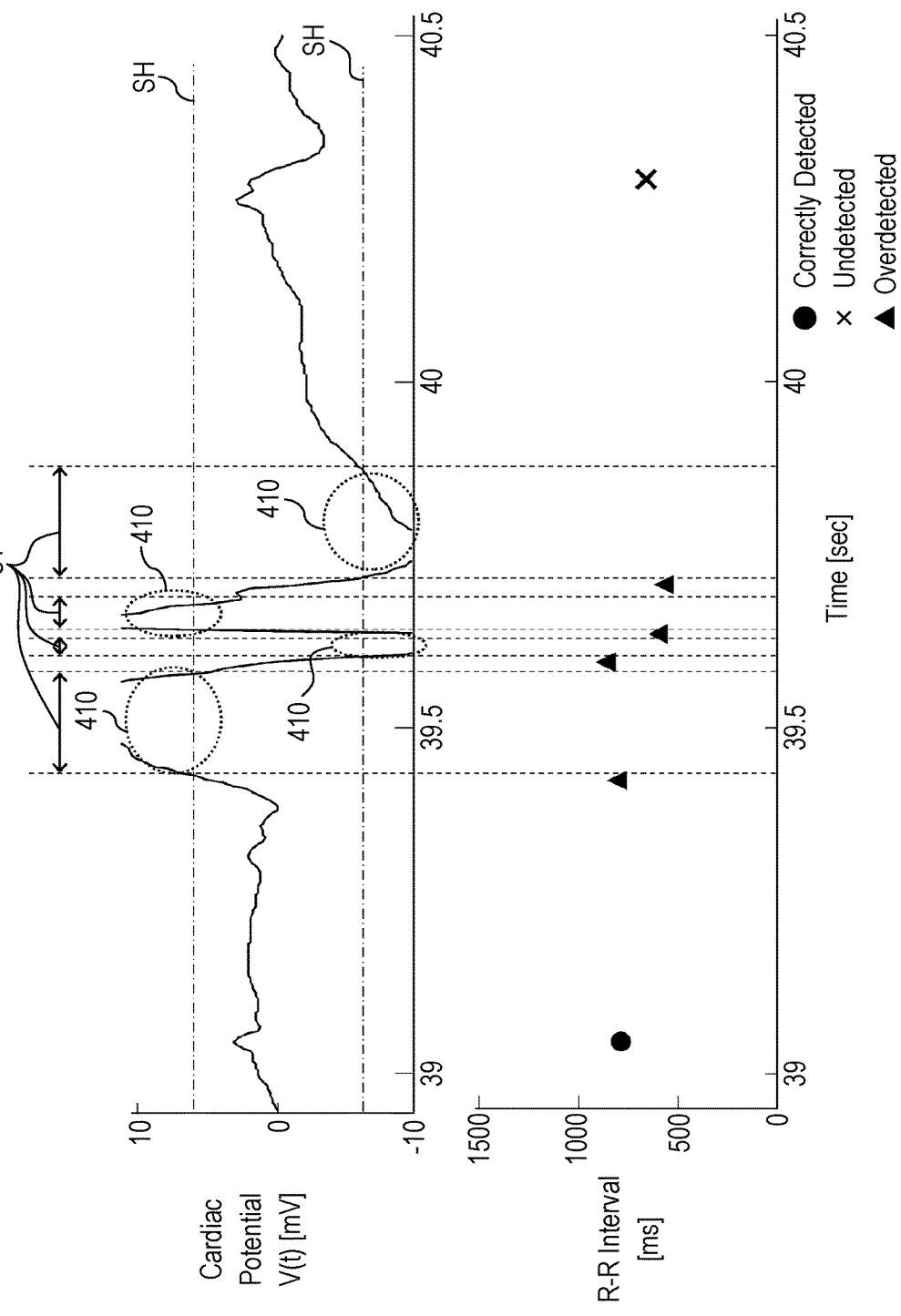
FIG. 9 shows an electrocardiographic waveform obtained by the cardiac potential detection device according to the exemplary embodiment, and R-waves detected when the transient period is 0 ms.

The influence of the transient period TT on the R-wave-detection performance will now be described as follows. FIG. 9 shows an ECG waveform obtained when the user bends his/her body sideways with belt 130 having electrodes pasted thereon around his/her chest, and R-waves detected when the transient period is 0 ms. The detection-suspension period ST coincides with each abnormal potential generation period 410 that exceeds the threshold SH. In this case, the steep changes between adjacent abnormal potential generation periods 410 in an ECG waveform are cases of R-wave overdetection (shown by triangles).

Figure 10:
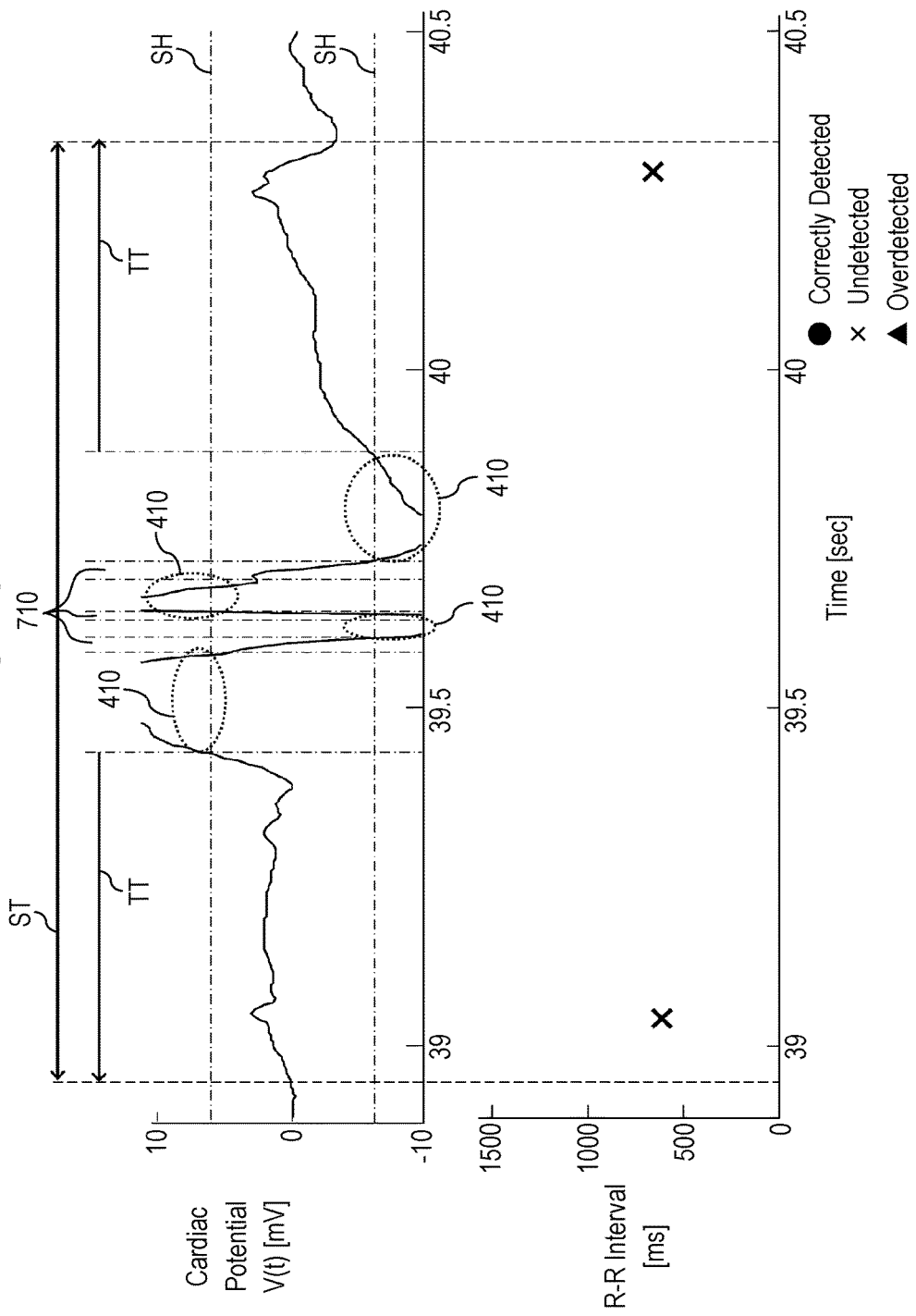
FIG. 10 shows an electrocardiographic waveform obtained by the cardiac potential detection device according to the exemplary embodiment, and R-waves detected when the transient period is 500 ms.

Meanwhile, FIG. 10 shows an ECG waveform obtained in the exemplary embodiment, and R-waves detected when the transient period is 500 ms. In FIG. 10 the detection-suspension period ST corresponds to abnormal potential generation periods 410 and the transient period TT before and after the periods 410. This reduces falsely detecting, as R-waves, steep changes occurring between adjacent abnormal potential generation periods 410 in an ECG waveform.

Figure 11:
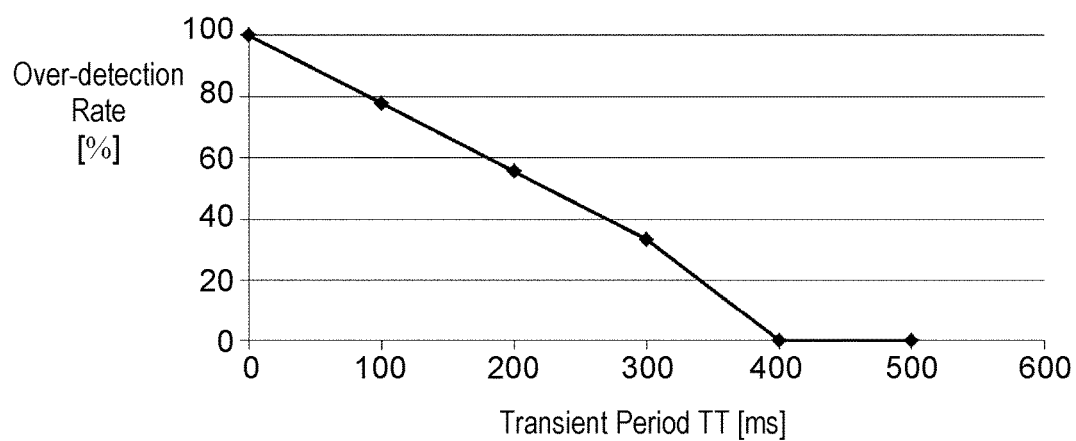
FIG. 11 shows the relationship between transient period and over-detection rate in the cardiac potential detection device according to the exemplary embodiment.

FIG. 11 shows the relationship between the transient period TT and the over-detection rate of R-waves. The horizontal axis represents the transient period TT, and the vertical axis represents the over-detection rate under the condition that the number of overdetected R-waves with a transient period TT of 0 ms is 100%, and that the transient period TT is changed at intervals of 100 ms. Increasing the transient period TT decreases the over-detection rate, and when the transient period TT is 400 ms, the over-detection rate is at its minimum. However, when the transient period TT is too long, the period of not detecting R-waves is too long. Therefore, it is preferable that the transient period TT should be about 400 ms.

As described above, in the present exemplary embodiment, cardiac potential detection device 100 includes electrodes 110 (right electrode 110a and left electrode 110b), and controller 200. Controller 200 detects an abnormal potential caused by changes in the condition of contact between of electrodes 110 and the user's body, and suspends R-wave detection in abnormal potential generation periods 410 and the transient period TT before and after each period 410. This achieves reducing R-wave overdetection.

The R-wave detection threshold is not updated in the detection-suspension period ST. This reduces the number of undetected R-waves, which is caused when the R-wave detection threshold is increased by the detection of an abnormal potential.

EXAMPLES

ECG waveforms acquired by cardiac potential detection device 100 according to the exemplary embodiment will be shown: one with disposable electrodes (Example 1), and the other with a shirt having conductive fiber electrodes pasted thereon (Example 2).

Example 1

Figure 12:
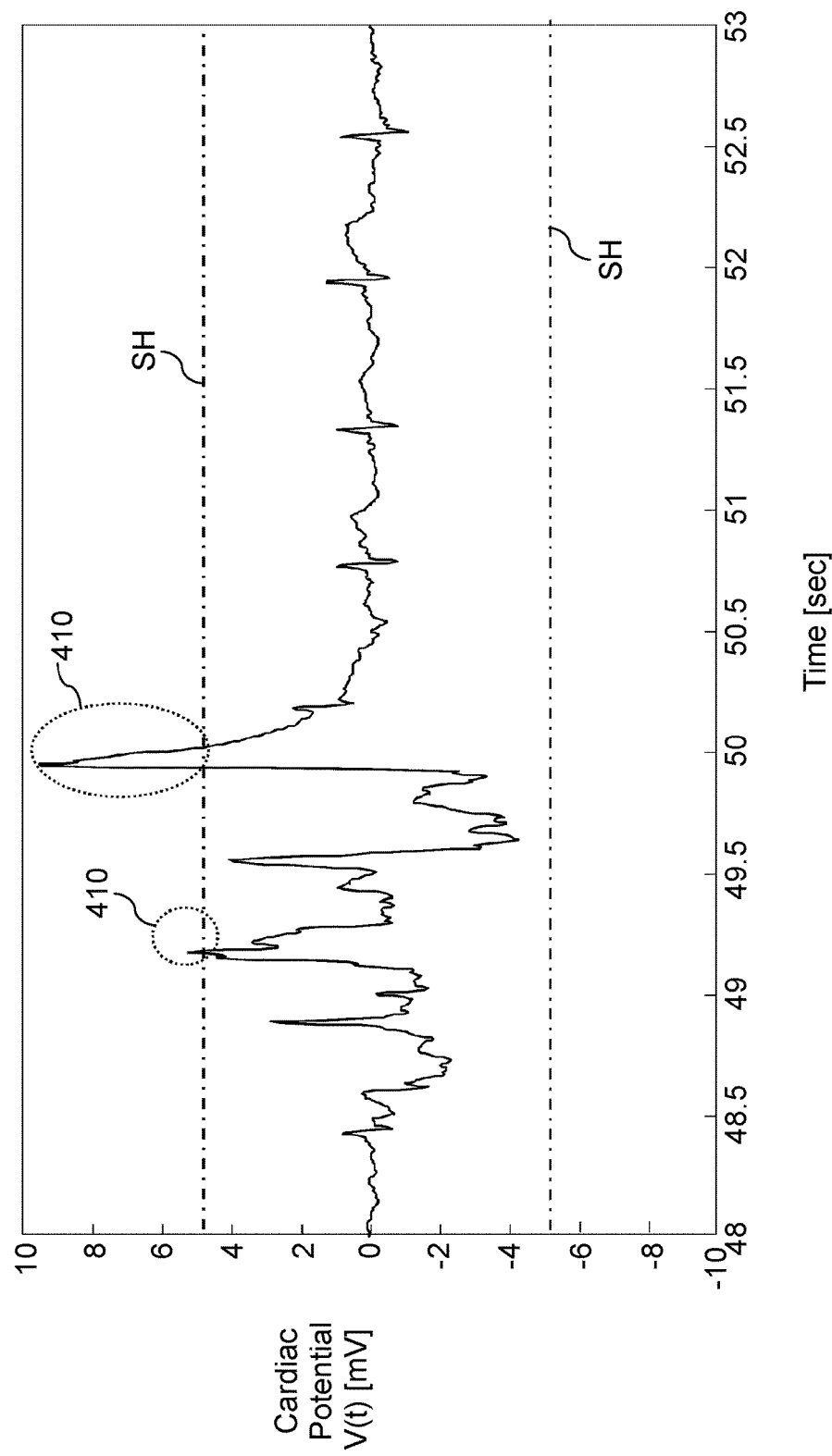
FIG. 12 shows an electrocardiographic waveform obtained in Example 1.

FIG. 12 shows an ECG waveform obtained in Example 1 when disposable electrodes were pasted on the user's skin. In FIG. 12 the user was found to have bent his/her body sideways in abnormal potential generation periods 410, and steep changes occurred in the ECG waveform due to changes in the condition of contact between the disposable electrodes and the user's skin.

Figure 13:
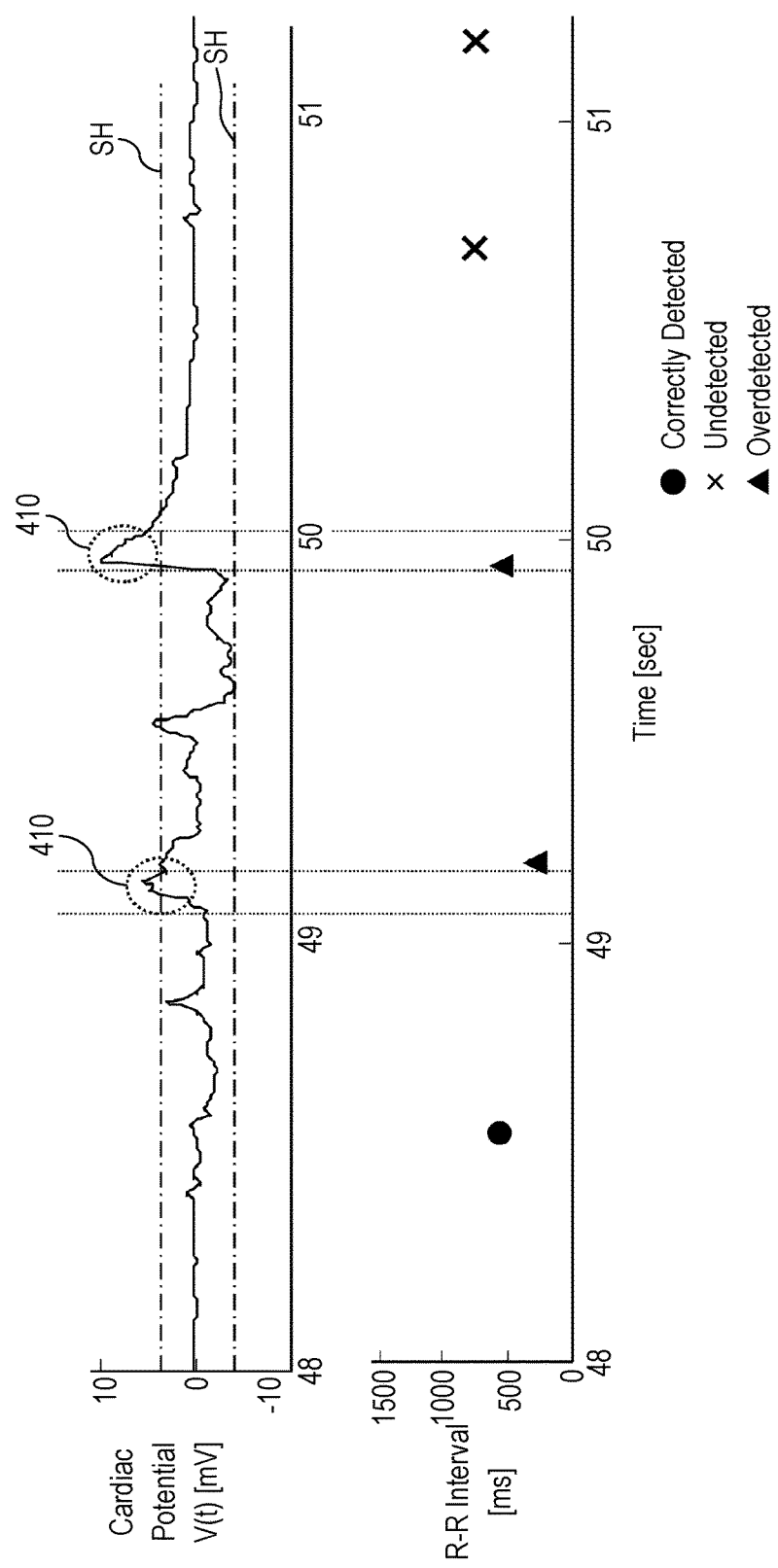
FIG. 13 shows an electrocardiographic waveform obtained in Example 1 and R-waves detected according to a conventional method.

FIG. 13 shows an ECG waveform obtained in Example 1, and R-waves detected in the case that R-wave detection was performed in all the periods without detecting an abnormal potential. In FIG. 13 two cases of R-wave overdetection (shown by triangles) occurred near abnormal potential generation periods 410, which were caused by changes in the condition of contact between electrodes 110 and the user's body, and later, two R-waves (shown by crosses) were left undetected.

The feature of R-waves changes with time depending on various factors (e.g., the user's physical condition, the condition of contact between the electrodes and the user's body, and the user's physical characteristics), so that the R-wave detection threshold is updated using the value at the time when the peak of the most recently detected feature appears. Therefore, if the R-wave detection threshold is updated and increased as a result that abnormal potentials are falsely detected as R-waves, then R-waves that should be detected are left undetected after the end of the abnormal potential.

Figure 14:
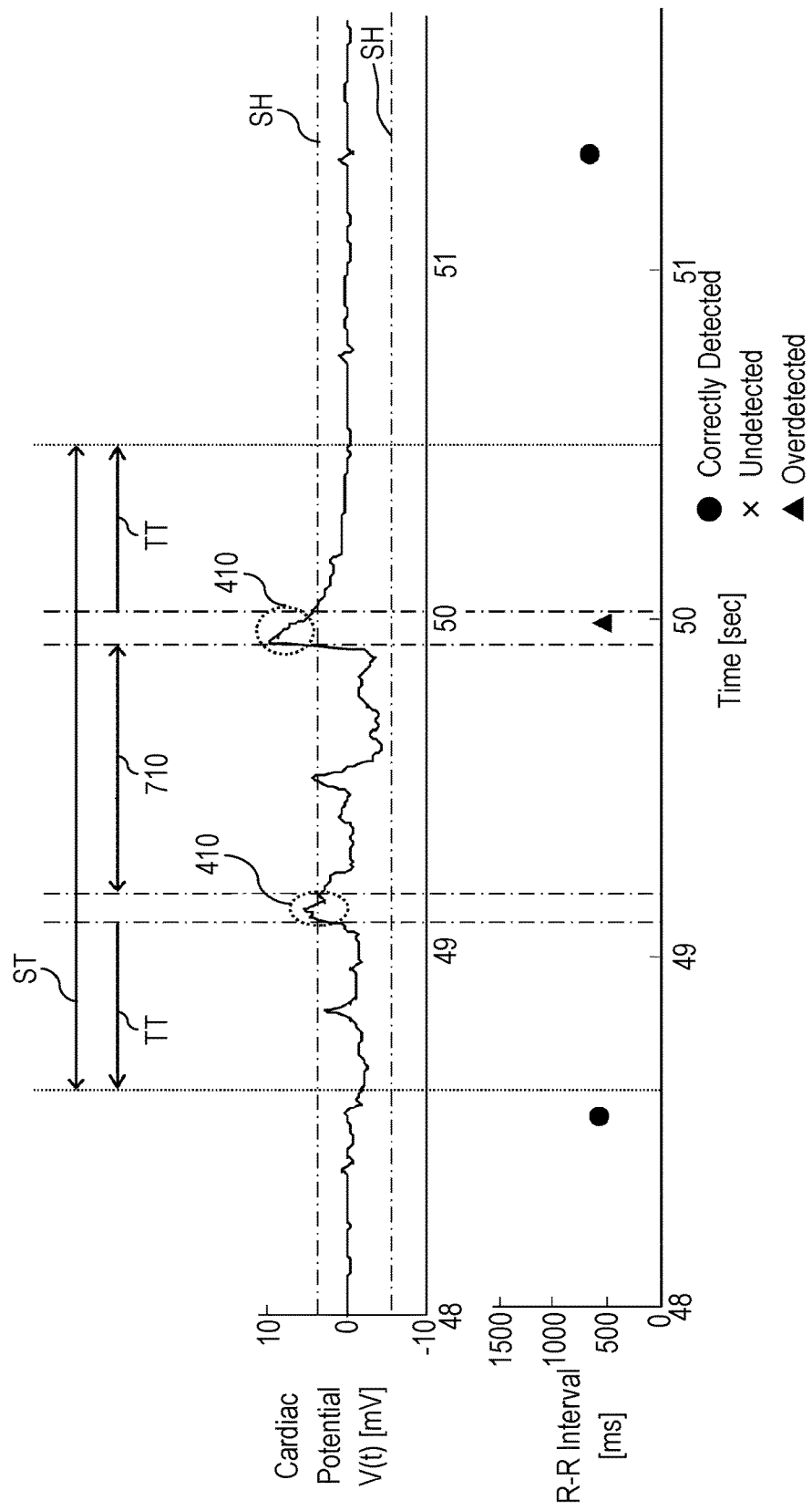
FIG. 14 shows an electrocardiographic waveform obtained in Example 1 and R-waves detected according to the present disclosure.

Meanwhile, FIG. 14 shows an ECG waveform obtained in Example 1, and R-waves detected according to the present disclosure when R-wave detection were suspended in abnormal potential generation periods 410 and in the transient period TT (500 ms) before and after each period 410. R-wave detection was suspended in the detection-suspension period ST shown in FIG. 14, so as to prevent falsely detecting, as R-waves, steep changes in an ECG waveform, which were caused when the user moved physically. The R-wave detection threshold was not updated because of the absence of R-wave overdetection, so that R-waves were correctly detected even after the end of the detection-suspension period ST.

As described above, in the case that the disposable electrodes were pasted on the user's skin, R-wave detection was suspended in abnormal potential generation periods 410 and the transient period TT before and after each period 410. This reduced falsely detecting, as R-waves, steep changes in the ECG waveform, which were caused when the user moved physically. This also reduced the number of undetected R-waves, which was caused when the R-wave detection threshold was increased as a result of the detection of an abnormal potential.

Example 2

Figure 15:
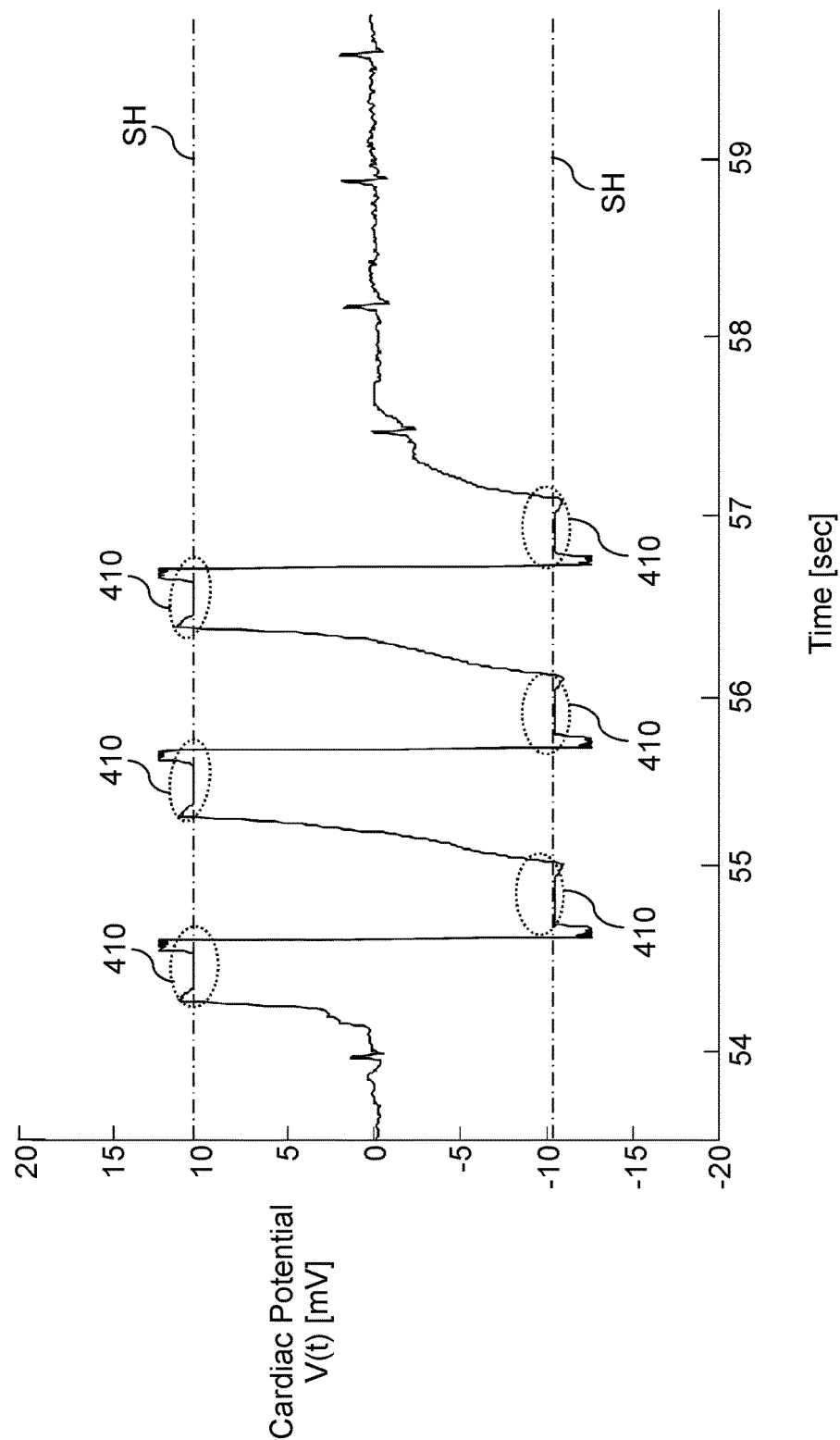
FIG. 15 shows an electrocardiographic waveform obtained in Example 2.

FIG. 15 shows an ECG waveform obtained in Example 2 when the user worn a T-shirt with conductive fiber electrodes pasted thereon. In FIG. 15, the user was found to have bent his/her body forward in abnormal potential generation periods 410 where steep changes occurred in the ECG waveform with changes in the condition of contact between the conductive fiber electrodes and the user's skin.

Figure 16:
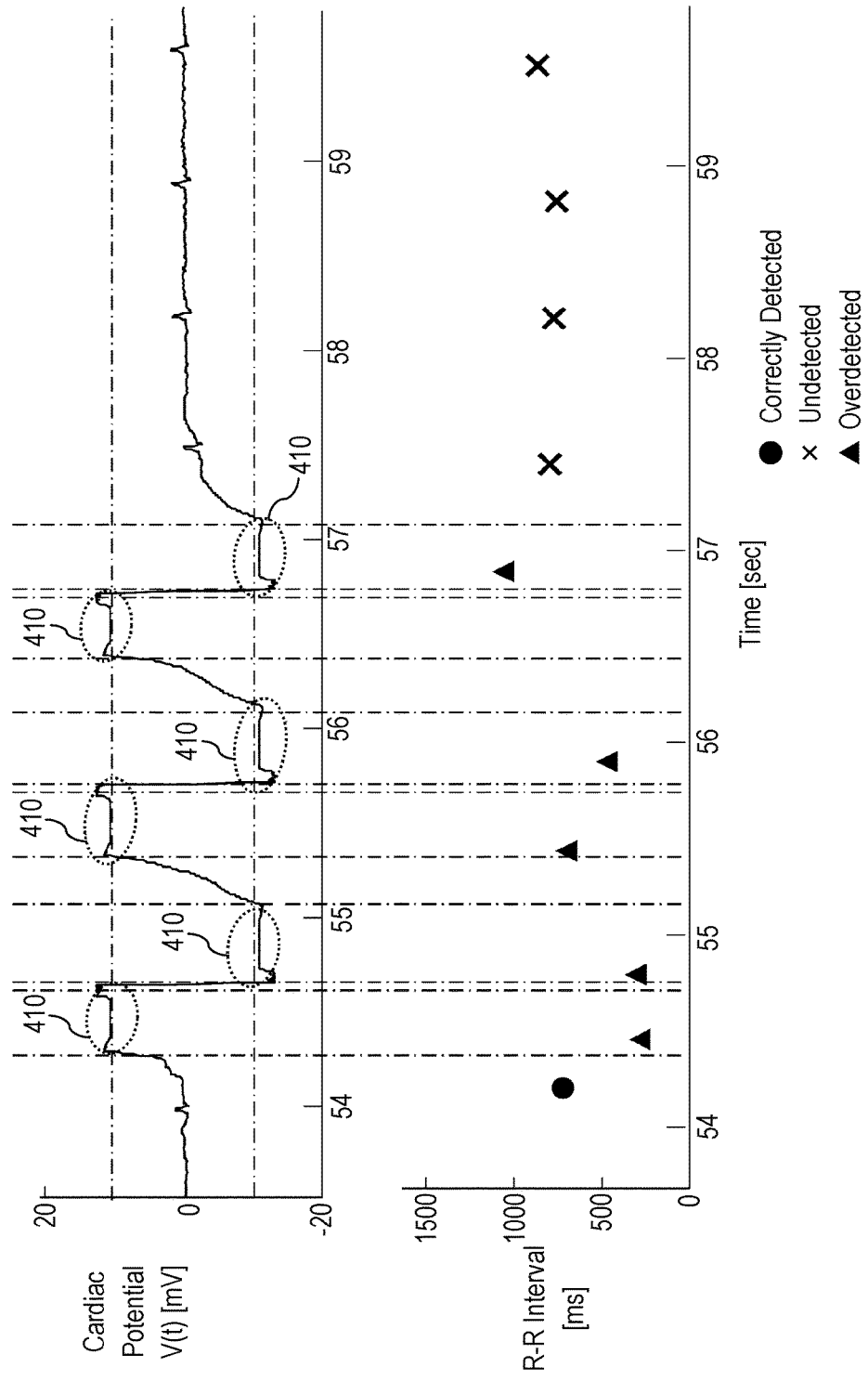
FIG. 16 shows an electrocardiographic waveform obtained in Example 2 and R-waves detected according to the conventional method.

FIG. 16 shows an ECG waveform obtained in Example 2, and R-waves detected without detecting an abnormal potential with the use of a threshold. Five cases of R-wave overdetection (shown by triangles) occurred near abnormal potential generation periods 410. In addition, four R-waves (shown by crosses) were left undetected at the end of abnormal potentials due to an increase in the R-wave detection threshold caused by R-wave overdetection.

Figure 17:
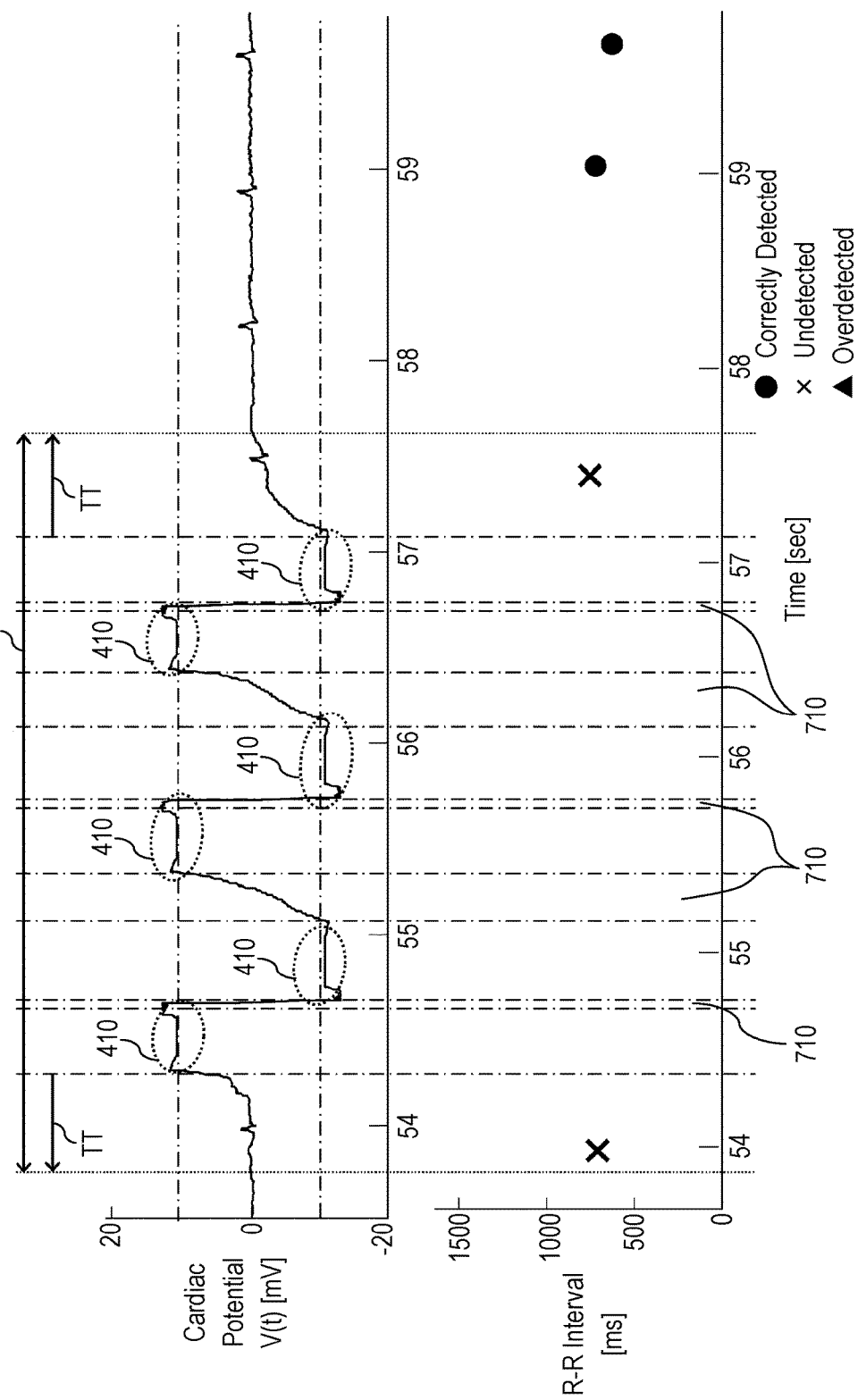
FIG. 17 shows an electrocardiographic waveform obtained in Example 2 and R-waves detected according to the present disclosure.

Meanwhile, FIG. 17 shows an ECG waveform obtained by cardiac potential detection device 100 according to the exemplary embodiment and R-waves detected in the case that R-wave detection was suspended in abnormal potential generation periods 410 and the transient period TT (500 ms) before and after each period 410. R-wave detection was suspended in the detection-suspension period ST shown in FIG. 17, so as to prevent falsely detecting, as R-waves, steep changes in an ECG waveform, which were caused when the user moved physically.

As described above, two R-waves were left undetected in the transient period TT because R-wave detection was suspended in this period. However, after the detection-suspension period ST expired, R-waves were detected correctly because there was no increase in the R-wave detection threshold as a result of the absence of R-wave overdetection.

It has been thus proved that even when an ECG waveform is acquired by making the user wear a T-shirt with conductive fiber electrodes pasted thereon, it is possible to prevent falsely detecting, as R-waves, steep changes in the ECG waveform caused when the user moves physically by suspending R-wave detection in abnormal potential generation periods 410 and the transient period TT before and after each period 410. This configuration also prevents an increase in the R-wave detection threshold caused by R-wave overdetection, thereby preventing undetected R-waves.

Figure 18:
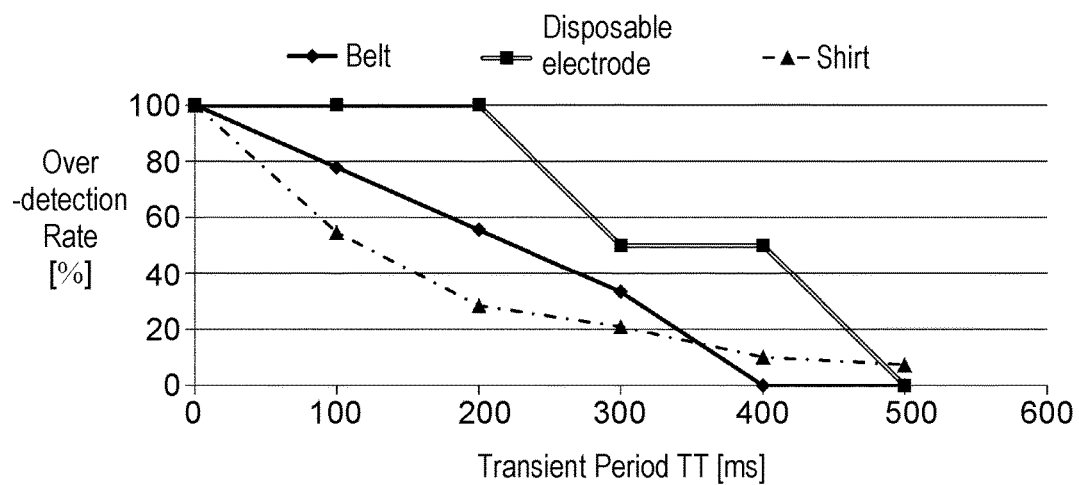
FIG. 18 shows the relationship between attachment media, transient period, and over-detection rate.

FIG. 18 shows the relationship between the over-detection rate and the transient period TT when electrodes 110 are attached to different attachment media. The horizontal axis represents the transient period TT, and the vertical axis represents the over-detection rate under the condition that the number of overdetected R-waves with a transient period TT of 0 ms is 100%, and that the transient period TT is changed at intervals of 100 ms. Regardless of the type of attachment medium to which electrodes 110 are attached, the over-detection rate is at its minimum when there is a transient period TT of 500 ms or so before and after each abnormal potential generation period 410. Hence, it is preferable that the transient period TT should be 500 ms or so.

The above-described exemplary embodiment exemplifies the techniques of the present disclosure. Therefore, various modification, replacement, addition, and omission can be made within the range of the claims and their equivalents.

INDUSTRIAL APPLICABILITY

The cardiac potential detection device according to the present disclosure is applicable to an electrocardiograph, a heart rate monitor, or other similar devices that can prevent falsely detecting, as R-waves, changes in the condition of contact between the electrodes and the user's skin.

REFERENCE MARKS IN THE DRAWINGS 100 cardiac potential detection device
110 electrode
110a right electrode
110b left electrode
120 wiring
130 belt (attachment medium)
200 controller
210 analog front end (AFE)
211 amplifier
212 A/D converter
220 control unit
221 band pass filter (BPF)
222 input potential detector
223 R-wave detector
230 memory
410 abnormal potential generation period
SH threshold
ST detection-suspension period
TT transient period

What is claimed is:

1. A cardiac potential detection device for detecting R-waves from an electrocardiographic waveform, the cardiac potential detection device comprising:
a plurality of electrodes;
a detector configured to detect an input voltage applied from the plurality of electrodes; and
a control unit configured to:
identify an R-wave candidate based on an R-wave detection threshold and a peak in the input voltage,
determine whether an absolute value of the input voltage is smaller than a predetermined threshold;
when the control unit determines that the absolute value of the input voltage has exceeded the predetermined threshold, calculate a detection-suspension period based on a time at which the input voltage exceeded the predetermined threshold, and suspend identifying of an R-wave candidate in the detection-suspension period, and
in a period excluding the detection-suspension period, identify the R-wave candidate as an R-wave when the input voltage does not exceed the predetermined threshold in a period from the R-wave candidate peak until a predetermined time expires.

2. The cardiac potential detection device according to claim 1, wherein the detection-suspension period includes a predetermined period occurring before the time at which the input voltage exceeded the predetermined threshold and a predetermined period after a time at which the input voltage has become and remains less than the predetermined threshold.

3. The cardiac potential detection device according to claim 1, wherein the control unit adaptively sets the R-wave detection threshold based on the input voltage in a period excluding the detection-suspension period, and keeps the R-wave detection threshold unchanged in the detection-suspension period.

4. The cardiac potential detection device according to claim 1, wherein the predetermined threshold is determined based on an input range of the detector.

5. The cardiac potential detection device according to claim 1, wherein the detection-suspension period includes a period of 500 ms occurring before and after the period in which the input voltage exceeds the predetermined threshold.

6. The cardiac potential detection device according to claim 1, wherein the plurality of electrodes are attached to an attachment to be worn by a human body.

7. The cardiac potential detection device according to claim 1, wherein the plurality of electrodes are attached to a gripping member.

8. A cardiac potential detection method for detecting R-waves from an electrocardiographic waveform, the cardiac potential detection method comprising:
detecting an input voltage applied from a plurality of electrodes;
identifying an R-wave candidate based on an R-wave detection threshold and a peak in the input voltage,
determining whether an absolute value of the input voltage is smaller than a predetermined threshold;
when the absolute value of the input voltage has exceeded the predetermined threshold, calculating a detection-suspension period based on a time at which the input voltage exceeded the predetermined threshold, and suspending identifying of an R-wave candidate in the detection-suspension period, and
in a period excluding the detection-suspension period, identifying the R-wave candidate as an R-wave when the input voltage does not exceed the predetermined threshold in a period from the R-wave candidate peak until a predetermined time expires.

9. The cardiac potential detection device according to claim 1, wherein the peak is a peak of the absolute value of a differential value of the input voltage.

* * * * *